(12) United States Patent
Frenoy

(10) Patent No.: US 7,335,354 B2
(45) Date of Patent: Feb. 26, 2008

(54) METHODS FOR THE REDUCTION OF MALIGNANT TUMORS BY AN EOSINOPHIL/HELMINTH THERAPY

(76) Inventor: George Frenoy, 863 Shorewood Dr., Bartlett, IL (US) 60103

( * ) Notice: Subject to any disclaimer, the term of this patent is extended or adjusted under 35 U.S.C. 154(b) by 385 days.

(21) Appl. No.: 10/914,475

(22) Filed: Nov. 24, 2004

(65) Prior Publication Data

US 2005/0163810 A1 Jul. 28, 2005

Related U.S. Application Data

(60) Provisional application No. 60/493,866, filed on Aug. 9, 2003.

(51) Int. Cl.
*A01N 63/00* (2006.01)
*A61K 45/06* (2006.01)
*A61K 45/08* (2006.01)

(52) U.S. Cl. .................... 424/93.7; 424/278.1

(58) Field of Classification Search .............. None
See application file for complete search history.

(56) References Cited

U.S. PATENT DOCUMENTS 6,071,517 A 6/2000 Fanger

2003/0026780 A1 2/2003 Hood
2003/0138433 A1 7/2003 Neweu

OTHER PUBLICATIONS

Mollnari et al (Int Arch Allergy Appl Immun, 1977, vol. 55, pp. 444-448).*
Tepper (J Allergy Clin Immunol, 1994, vol. 94, pp. 1225-1231).*
Taylor et al (Int J Oncol, Dec. 1998, vol. 13, pp. 1305-1311).*
J. Mattes et. al. 'Immunolotherapy of cytotoxic T cell risitant tumors by Th2 cells: an eotaxin and stat6 dependant process' J. Exp. Med. Feb. 3, 2003. 197(3):387.93.
Pretlow TP, Keith EF, et. al. 'Eosinophil infiltration of human colonic carcinomas as a prognostic indicator' Pubmed 6850611 indexed for medline, June 1983.
DR. Timothy Lee 'Eosinophils an tumor cytotoxicity' microbiology. medicne.dal.ca/immunolgy/tumor/canceo.htm, downloaded May 9, 2003.
Inhabition of cancer cell growth by activated eosinophils Furbert-Harris P, Parish-Gause D, Lanty An I, et.al. Prostate 57:165-175 (2003).

* cited by examiner

*Primary Examiner*—Karen A. Canella

(57) ABSTRACT

The invention is a method of reducing malignant tumor sizes in mammals by eliciting activated eosinophils to infiltrate the tumor by using helminth excretory and secretory antigens, helminth ova, and helminth extracts, in such a way that the immunological response to the malignant tumor is as if were responding to a helminth.

6 Claims, 1 Drawing Sheet ately large malignant tumors they fail to, as it seems, recognize important aspects about eosinophils, as a strategic arm of the immune system, in effectively fighting

METHODS FOR THE REDUCTION OF MALIGNANT TUMORS BY AN EOSINOPHIL/HELMINTH THERAPY

This application claims the benefit of U.S. Provisional Application No. 60/493,866, filed Aug. 9, 2003.

CROSS-REFERENCE TO RELATED APPLICATIONS

Not applicable

STATEMENT REGARDING FEDERALLY SPONORED RESEARCH OR DEVELOPMENT

Not applicable

REFERENCE TO SEQUENCE LIST, A TABLE, OR COMPUTER PROGRAM LISTING COMPACT DISK APPENDIX

Not applicable

BACKGROUND FOR THE INVENTION

The present invention is a method that generally relates to the reduction in size of malignant tumors in mammals, more particularly lab rodents, pets domestic mammals, and other mammals not excluding humans. Reducing antigenic load by surgery or chemotherapy in lab animals, pets and domestic animals is cost prohibitive and in many cases is ineffective.

Current therapies do not address important aspects in the pathogenesis of cancer.

One of the main reasons, besides size, why a malignant tumors persist in the face of immunolgical onslaught is because of the shedding of antigen from the cancer cells in excess with attacking antibodies form antigen-antibody complexes, blocking further attack from the immune system (page 149 FIG. 8-15 'Essential Concepts in Immunology'). (page 245 FIG. 8:14 'Essential Immunology').

This process further results in suppressing the response and works towards establishing tolerance of the malignant tumor (page 149 FIG. 8-16 'Essential Concepts in Immunology'), (Science, vol. 257 Aug. 21, 1992 pages 1130-1133).

Other immunotherapies fail because these therapies attempt to employ mostly, via vaccines and other modes, macrophages, neutriphils, killer cells, and cytotoxic t cells, which are equipped to eliminate smaller pathogens. Although these cells are needed in the total response, they are by themselves ineffective against targets that are too large and that are immunolgically shielded by antigen antibody complexes. While macrophages do phagocytose antigen and antibody complexes, their minor presence as infiltrates inside tumors, for the most part, is for the purpose of cleaning up cellular debris. Under normal circumstances their activity in the tumor is at the least negligible and at the worst counterproductive as they would help maintain the viability of tumor cells by clearing away cellular debris.

While some research groups have come to appreciate activated eosinophils as a potentially important tool in reducing the size of malignant tumors they fail to, as it seems, recognize important aspects about eosinophils, as a strategic arm of the immune system, in effectively fighting pathogens that measure up to a profile very similar to that of malignant tumors. Therefore they fail to fully exploit this advantage.

This invention is a method for reducing malignant tumors by using activated eosinophils, a type of white blood cell elicited by helminth (a multi-cellular parasite) antigen.

This method addresses an important aspect in the pathogenesis of cancer namely size, immunolgical shielding and evasion.

It addresses this aspect by eliciting activated eosinophils to the tumor site and causing them to respond along with the other immunocytes to respond to the tumor as if it were a helminth.

Eosinophils are strongly associated with the Th 2 immune response and because they are capable of both phagocytsising antigen and antibody complexes (Clinical and Basic Immunology 1977 edition page 285) and antibody cell-mediated cytotoxicty (ADCC) they have ease of access to and into the tumor. And as they are functionally equipped to fight helminths which present similar strategy criteria as malignant tumors (size, immunological shielding and evasion) they meet the necessary strategic requirements in reducing tumor size in mammals.

Furthermore, because helminth excretory and secretory helminth antigens elicit such a pronounced Th2 immune response, that they cause bystander (Eur. J. Immunol. 2000. 30: pg. 1977-1986 J. Holland et. al.) antigens (tumor) responses to also be driven to a Th2 response. This results in the mammal immunolgically responding to the tumor as if it were a helminth.

BRIEF SUMMARY OF THE INVENTION

This invention is a method for reducing malignant tumors by using activated eosinophils, a type of white blood cell, elicited by helminth (multicellullar parasite) antigens. This method addresses a important aspect in the pathogenesis of cancer namely size, and immunological shielding. It addresses this aspect by the elicitation of activated eosinophils to the tumor site and also by immunolgically modulating the response to the tumor to a TH2 mode and profile so that the tumor is responded to as if it were a helminth. This result can be accomplished in a number of ways, but not limited by the following list.

1. By injecting helminth heat liable secretory and excretory antigens into the tumor and repeating as necessary.
2. By injecting helminth dead helminth eggs, into the tumor, and repeating as necessary,
3. By injecting helminth extracts, into to the tumor, and repeating as necessary,
4. By injecting different species of helminth antigen and or dead helminth eggs, into to the tumor, and repeating as necessary,
5. By injecting live attenuated helminths into the tumor site;
6. By elevating serum levels of eosinophils by helminth challenge and then injecting helminth antigens into the tumor site.
7. By elevating serum levels of eosinophils by helminth challenge and then injecting helminth antigens into the tumor site along with interlukin-4 and eotaxin.

DETAILED DESCRIPTION

Figure 1:
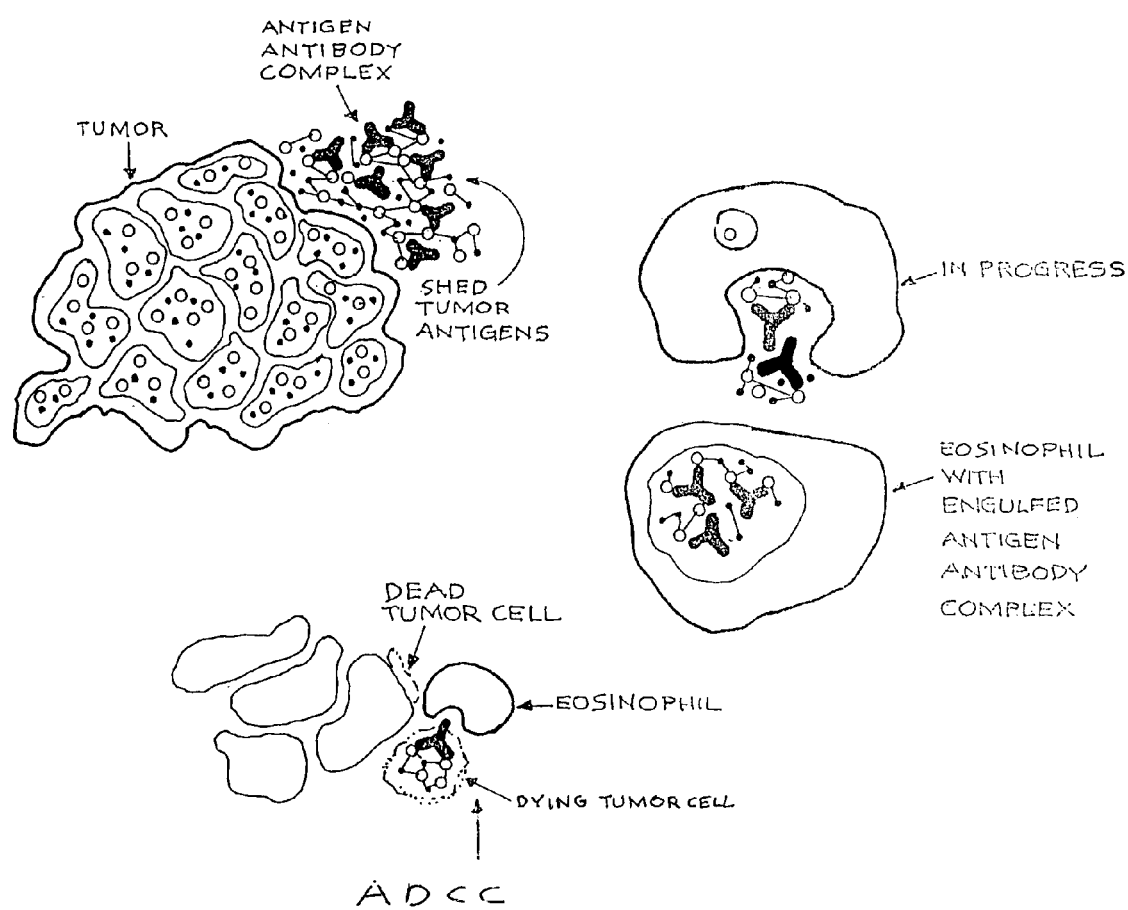
FIG. 1: At 11 oclock we see the tumor shedding antigen, forming antigen-antibody complexes with attacking antibodies. At 3 o'clock we see an eosinophil engulfing antigen-antibody complexes. At 7 o'clock we see eosinophil infiltrating and killing tumor cells by antibody dependent cell mediated cytotoxicity.

The term helminth antigen used here means heat liable excretory and secretory proteins obtained from live helminths in vitro.

The term helminth means a multi-cellular parasite.

The term helminth extract means any protein extracted from helminths.

The term helminth ova means eggs that are from helminths.

Eosinophil serum levels means the amount of eosinophil in the blood, eosinophils normally comprise about 1-3% of circulation leukocytes.

The term solid malignant tumor is defined as a mass of malignant or cancerous tissue whose cells have lost resemblance to normal cells, and that is marked by aberrant, pathological and invasive growth into normal tissue without inhibition to normal anatomical boundaries.

The eosinophil is a type of white blood cell that when activated will engulf antigen and antibody complexes and that will also kill pathogens with (adcc) antibody dependent cell mediated cyctotoxicity, whereby it latches on to the fc region or tail end of the antibody that is attached to the antigen on the surface of the pathogen and then poisons the pathogen.

Eotaxin is a chemotactic factor or a substance that activates and attracts eosinophils to where the eotaxin is located.

An activated eosinophil is an eosinophil that has been primed to fully carry out its function by cytokines or immunological messengers.

Interleukin 4 (IL-4) is a cytokine.

Antigen is a substance that can incite the production of specific antibodies which combine with that antigen.

Antibody is a protein secreted by B-cells or plasma cells and that combines with a specific antigen.

Helminth Excretory and Secretory proteins as used here are proteins secreted by helminth parasites in vitro or grown in a culture medium and that are heat sensitive.

Inject as used here means to administer or force a fluid preparation into a tumor site by means of a syringe with a very fine gauged needle.

Preparation means here a pharmecutical grade purity and quality for use in humans.

Live attunuated helminths that have been irratiated or compromised by some other means to such an extent that the ability to infect is severely limited.

A preferred embodiment of the present invention but not limited to, include the use of heat liable, excretory and secretory helminth proteins (HES) as the helminth antigen. The helminth as exemplified, but not limited to, is Nippostrongylus Brasiliensis. The mammal as exemplified, but not limited to, is a wild or lab mouse with a malignant solid tumor as exemplified by but not limited to carcinoma. Pursuant to the invention, heat liable excretory and secretory proteins (HES) are can be prepared, but not limited to, by following the protocol as described by M. J. Holland et. al. (Eur. J. Immunol. 2000. 30: page 1984 J. Holland et. al.) or (Rev. Inst. Med. trop S. Paulo Vol. 39 n.5 Sao Paulo/October 1997 Materials and Methods for TES) administer intratumorally about 5 micro grams-1 mg HES antigen in for a tumor the size of 27 cubic millimeters, preferably amount 75 micrograms. Repeat injections every 2-8 days as necessary. Those skilled in the art will be able to necessary adjustments of amount of HES to tumor size and type and to the specific mammal following the pattern of example described here.

Another embodiment, pursuant to the invention, is to use about 10,000 aneseptically washed helminth eggs as exemplified in, but not limited to, the species of *Schistosoma mansoni* that have been suspended in PBS (phosphate buffer saline) and stored in liquid nitrogen and freeze/thawed-killed. The mammal as exemplified, but not limited to, is a wild or lab mouse with a malignant solid tumor as exemplified by but not limited to carcinoma. Inject intratumorally for a tumor about the size 27 mm. Those skilled in the art will be able to necessary adjustments of amount of eggs to tumor size and type and to the specific mammal following the pattern of example described here.

Another embodiment is using helminth extract obtained using the protocol described (Braz J Biol Res January 2002 Vol. 1 81-89 Mat. and Meth.) and injecting about 0.1 ml intratumorally for a tumor about the size 27 mm. The mammal as exemplified, but not limited to, is a wild or lab mouse with a malignant solid tumor as exemplified by but not limited to carcinoma. Those skilled in the art will be able to necessary adjustments of amount of extract to tumor size and type and to the specific mammal following the pattern of example described here.

Another embodiment is to elevate serum level with helminth extract challenge until activated eosinophil level reaches at least 20%+ and then inject that same species HES antigen 5 micro grams-1 mg intratumorally for a tumor about the size 27 mm. The mammal as exemplified, but not limited to, is a wild or lab mouse with a malignant solid tumor as exemplified by but not limited to carcinoma. Those skilled in the art will be able to necessary adjustments of amount of antigen to tumor size and type and to the specific mammal following the pattern of example described here.

Another embodiment is to elevate serum level with helminth extract or antigen challenge until activated eosinophil level reaches at least 20%+ and then inject that same species HES antigen 5 micro grams-1 mg in solution with 0.001 U-5,000 U interleukin 4 and 0.01-500 micrograms eotaxin intratumorally for a tumor about the size 27 mm. The mammal as exemplified, but not limited to, is a wild or lab mouse with a malignant solid tumor as exemplified by but not limited to carcinoma. Those skilled in the art will be able to necessary adjustments of amounts for the preparation in accordance with the tumor size and type and to the specific mammal following the pattern of example described here.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A method for reducing tumor size by inducing eosinophil infiltrates within said tumor by elevating eosinophil serum levels with helminth antigen and then later by injecting that same helminth antigen, extract or killed ova into said tumor.

2. A method for reducing tumor size by inducing eosinophil infiltrates within said tumor by elevating eosinophil serum levels with helminth extract and then later by injecting that same helminth antigen, extract or killed ova into said tumor.

3. A method for reducing tumor size by inducing eosinophil infiltrates within said tumor by elevating eosinophil serum levels with helminth antigen and then later injecting either helminth antigen, extract or killed ova in a preparation with eotaxin and il-4 into said tumor.

4. A method for reducing tumor size by inducing eosinophil infiltrates within said tumor by elevating eosinophil serum levels with helminth extract and then later injecting helminth antigen, extract or killed ova in a preparation with eotaxin and il-4 into said tumor.

5. A method for reducing tumor size by inducing eosinophil infiltrates within said tumor by injecting killed ova into said tumor.

6. A method for reducing tumor size by inducing eosinophil infiltrates within said tumor by injecting helminth excretory and secretory proteins into said tumor.

* * * * *